United States Patent [19]
Nisch

[11] Patent Number: 6,032,062
[45] Date of Patent: Feb. 29, 2000

[54] MICROELECTRODE ARRANGEMENT

[75] Inventor: Wilfried Nisch, Tubingen, Germany

[73] Assignee: NMI Naturwissenschaftliches und Medizinisches Institut, Germany

[21] Appl. No.: 09/000,268

[22] PCT Filed: Aug. 1, 1996

[86] PCT No.: PCT/DE96/01428

§ 371 Date: Mar. 24, 1998

§ 102(e) Date: Mar. 24, 1998

[87] PCT Pub. No.: WO97/05922

PCT Pub. Date: Feb. 20, 1997

[30] Foreign Application Priority Data

Aug. 10, 1995 [DE] Germany ............ 195 29 371

[51] Int. Cl.$^7$ .................................................. A61N 1/04
[52] U.S. Cl. .......................... 600/372; 600/373; 607/54; 607/116; 607/148
[58] Field of Search ............................ 600/372, 373, 600/381; 607/116, 117, 148; 204/403; 435/287.1

[56] References Cited

U.S. PATENT DOCUMENTS

| | | |
|---|---|---|
| 3,848,608 | 11/1974 | Leonard . |
| 4,461,304 | 7/1984 | Kuperstein . |
| 4,969,468 | 11/1990 | Byers et al. ............... 128/642 |
| 5,016,633 | 5/1991 | Chow . |
| 5,024,223 | 6/1991 | Chow . |
| 5,178,161 | 1/1993 | Kovacs . |
| 5,215,088 | 6/1993 | Normann et al. ........... 128/642 |
| 5,397,350 | 3/1995 | Chow et al. . |
| 5,556,423 | 9/1996 | Chow et al. ................ 607/54 |
| 5,810,725 | 9/1998 | Sugihara et al. ........... 600/372 |
| 5,873,901 | 2/1999 | Wu et al. .................... 607/54 |
| 5,895,415 | 4/1999 | Chow et al. ................ 607/54 |

FOREIGN PATENT DOCUMENTS

| | | |
|---|---|---|
| 0689051 | 12/1995 | European Pat. Off. . |
| 3813838 | 5/1989 | Germany . |
| 4013188 | 11/1990 | Germany . |
| WO9639221 | 12/1996 | WIPO . |

OTHER PUBLICATIONS

Gerhard Wiegleb, "Sensortechnik", Franzis Elektronik—Fachbuch, pp. 141–144, 1986.

German Textbook "Lehrbuch der Experimentalphysik", dated 1987, pp. 664–669.

*Primary Examiner*—Linda C. M. Dvorak
*Assistant Examiner*—David M. Ruddy
*Attorney, Agent, or Firm*—Bachman & LaPointe, P.C.

[57] ABSTRACT

The invention concerns a microelectrode arrangement for leaking, with local resolution, electrical cell potentials, or for electrical stimulation of networks of biological cells such as for example cell cultures, tissue slices "in vitro" or biological tissue "in vivo". In order to attain high local resolution and high temporal resolution, the invention suggests that, as microelectrodes ($M_1$ to $M_n$), in each instance a contacting electrode ($K_1$ to $K_n$) be placed above a pad electrode ($A_1$ to $A_n$) onto a substrate (S); with light-sensitive elements, preferably in the shape of a continuous layer (P) arranged between the said contacting electrodes and the pad electrodes. By illuminating the light-sensitive layer (P) in the region of individual microelectrodes ($M_1$ to $M_n$), these microelectrodes are selected. Selection is preferably by the transmitted-light process through the substrate (S). In this case, substrate (S) and pad electrodes ($A_1$ to $A_n$) must be translucent. For selection by means of impinging light, the contacting electrodes ($K_1$ to $K_n$) are constructed in a translucent way (FIG. 1b).

15 Claims, 3 Drawing Sheets

MICROELECTRODE ARRANGEMENT

The invention concerns a microelectrode arrangement for locally-resolved, in particular extracellular, leakage measurement of electrical cell potentials or for electrical stimulation of networks of biological cells.

Biological cells or networks of biological cells such as for example cell cultures, tissue slices "in vitro" or biological tissue "in vivo" in electrophysiology are usually contacted by glass microelectrodes with electrolyte filling, or by metal microelectrodes. The electrodes are inserted into a cell by means of a so-called micromanipulator (intracellular process), brought into close contact with a cell membrane (patch clamp process), or brought into the vicinity of the cell membrane (extracellular process) so that the microelectrodes are connected in an electrically-conductive way to the biological cells of the network by way of an electrolyte solution. The disadvantage of these contacting processes is that only one, or with great expense, only a few cells can be contacted simultaneously and as a result, no network characteristics can be examined.

For this reason attempts have been made in recent times to contact a network of biological cells at many places concurrently, by means of microstructured microelectrodes deposited onto a substrate (carrier) by methods known from microelectronics, to leak electrical cell potentials in an extracellular way or to be able to electrically stimulate the cells. In this, the microelectrodes should be arranged in the highest possible density in order to achieve high local resolution. Furthermore, the electrical potentials of the cells should be leaked as far as possible simultaneously, i.e. in a parallel way, or electrical potentials for stimulating the network should be able to be applied to these cells simultaneously, in order to achieve a high temporal resolution.

There is however the problem that electrical leads from the individual microelectrodes have to be conducted in an insulated way right up to an electronic device for measuring or stimulation, or similar. The multitude of parallel leads insulated from each other limits the local resolution of the microelectrode arrangement.

Another option is, for each microelectrode to accommodate an integrated electronic switch on the substrate and to connect (select) the microelectrodes to the measuring or stimulation electronics by multiplex operation individually or in groups, in time sequence. This necessitates very great expense in integrated circuit engineering (VLSI technology) and thus considerably increases the cost of the microelectrode arrangement. In addition, the local resolution remains limited, due to the electronic switches which need to be accommodated on the substrate. Furthermore, the microelectrodes can no longer be selected concurrently, but only individually or in groups in sequence; the temporal resolution of the leakage or stimulation is reduced. Interference voltages are a further disadvantage; when switching, they can be transmitted by the electronic switches to the microelectrodes and to their connecting leads and can be superimposed on the measuring signal. Such interference voltages negatively influence the measurement result and the signal-to-noise ratio. Interference voltages can exceed the measuring signal many times, therefore their decay must be awaited after switching, before any measurements or stimulation can take place at all. This further reduces the temporal resolution of the microelectrode arrangement.

The number of microelectrodes of known microelectrode arrangements is therefore limited (less than 100 microelectrodes).

It is thus the object of the invention to provide a microelectrode arrangement of the type mentioned in the introduction, with a very large number of microelectrodes which as a result of small dimensions of the microelectrodes and small spacing from each other allows a high local resolution and in addition a high temporal resolution.

This task is solved by the characteristics of claims 1 and 9. Each microelectrode of the microelectrode arrangement according to the invention comprises a contacting electrode, a connection for an electronic device for measuring or stimulation, or similar, below referred to as a "pad electrode", as well as a light-sensitive element.

By way of an electrolyte solution, the contacting electrode can be brought into electrically conducting contact with a biological cell of a network. This preferably takes place in that the microelectrode arrangement is brought to a network of biological cells and thus the microelectrodes are brought into close proximity of cell membranes, i.e. in an extracellular way. In this, an electrical transition resistance (impedance) exists between the cells and the microelectrodes.

The light-sensitive element which in darkness has a very high electrical resistance which is reduced when it is exposed to light (or vice versa), is arranged between the contacting electrode and the pad electrode; the said light-sensitive element serves as a switch insulating the contacting electrode from the pad electrode or connecting it with the pad electrode as an ohmic resistance. This switch is activated by directing light onto it, i.e. onto the light-sensitive element. Thus each microelectrode is individually selectable by light; the microelectrodes of the microelectrode arrangement according to the invention can be addressed by light.

The invention provides the advantage that its microelectrodes are of very small dimensions and can be arranged very closely beside each other, thus a high local resolution can be achieved. The invention provides a further advantage in that the microelectrodes can be selected simultaneously, i.e. in a parallel way, individually or in groups, thus allowing high temporal resolution. A further advantage is provided in that due to selection by light, no interference voltages occur which are superimposed onto the measurement signal, and the decay of which would have to be awaited prior to taking a measurement or undertaking a stimulation.

The contacting electrodes, the light-sensitive element and the connecting electrodes can be arranged in two or three planes above each other or else in one plane beside each other, on a substrate. The arrangement in three planes above each other results in the most closely spaced arrangement of the microelectrodes, and thus provides the highest local resolution.

The light-sensitive element which preferably when it is not impinged by light, i.e. when it is dark, provides electrical insulation, can serve to insulate the contacting electrodes and the pad electrodes of the various microelectrodes from each other. In this case, the light-sensitive element is designed as a continuous layer common to all microelectrodes or to groups of microelectrodes onto which light is directed which is locally limited to the microelectrodes to be selected. In this case, either the contacting electrode or the pad electrode and the substrate onto which the microelectrodes are deposited, must be translucent for selection by light.

If the light-sensitive elements are arranged beside the contacting electrodes or beside the connecting electrodes, then the contacting electrodes and the pad electrodes can be made light impermeable, from the same material and deposited onto the substrate in one work process.

The pad electrodes of all microelectrodes or of groups of the microelectrodes can be combined in a common pad electrode. In this way the required number of connecting leads is reduced, however the microelectrodes can no longer be selected in parallel but only in series or parallel in groups.

In order to select the microelectrodes, one embodiment of the invention provides for fibreoptics which preferably comprise the same number of optic fibres as there are microelectrodes in the arrangement, so that one optic fibre leads to each microelectrode. In this, the front ends of the optic fibres from which light emanates can serve as the substrate for the microelectrodes.

In a further development of the invention, the fibreoptics comprise a light source for each optic fibre. Preferably the light sources are light-emitting diodes which are combined to form a matrix.

The microelectrode arrangement according to the invention can be implanted for leaking impulses or for electrical stimulation of nerve cells in plants or living things. For example, the microelectrode arrangement according to the invention can be used as a retina implant.

Focused light, for example a laser beam, is used to select certain microelectrodes of the arrangement according to the invention. Patterns of light spots, light beams or similar can be projected onto the arrangement in order to simultaneously select particular microelectrodes.

Below, the invention is explained in greater detail by means of an exemplary embodiment, as follows.

Figure 1A:
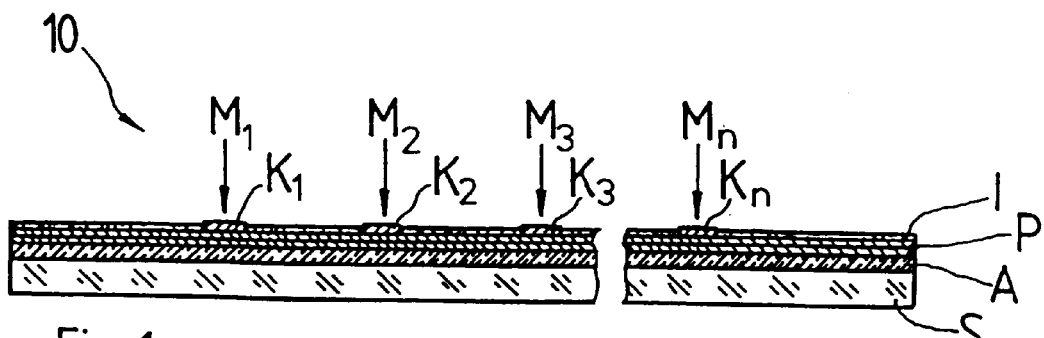
FIG. 1 shows a section through a microelectrode arrangement according to the invention with microelectrodes to be selected in series (FIG. 1a) or in parallel (FIG. 1b)

The microelectrode arrangement 10, according to the invention, shown in FIGS. 1a and b has been deposited onto a substrate S. Preferably, the substrate S comprises a translucent material, such as for example glass or plastic. It can however also comprise a non-translucent material such as for example ceramics or silicon with oxide layer insulation, as is known for example from microelectronics.

The microelectrodes $M_1$ to $M_n$ comprise pad electrodes A, $A_1$ to $A_n$, light-sensitive elements P and contacting electrodes $K_1$–$K_n$, which have been deposited as thin-film elements onto the substrate S on top of each other in three planes in the order mentioned. With serial selection of the microelectrodes $M_1$ to $M_n$, a single, continuous pad electrode A, shared by all microelectrodes $M_1$ to $M_n$, can be deposited onto the substrate S (FIG. 1a). With parallel selection, each microelectrode $M_1$ to $M_n$ comprises a pad electrode $A_1$ to $A_n$, which are all separated from each other by an insulating layer I. The insulating layer I has been deposited in one layer with the pad electrodes $A_1$ to $A_n$, onto the substrate S.

The light-sensitive elements have been deposited as a continuous layer P in common for all microelectrodes $M_1$ to $M_n$, onto the pad electrodes A, $A_1$ to $A_n$ and if applicable to the insulating layer I. Contacting electrodes $K_1$ to $K_n$, which during parallel selection are located above the pad electrodes $A_1$ to $A_n$, have been deposited onto the layer P constituting the light-sensitive elements. The contacting electrodes $K_1$ to $K_n$ which have been deposited onto the light-sensitive layer P in a plane with the contacting electrodes $K_1$ to $K_n$ are also separated from each other by an insulating layer. The contacting electrodes $K_1$ to $K_n$ protrude slightly above their insulating layer I.

The contacting electrodes $K_1$ to $K_n$, designed as thin-film elements, the light-sensitive elements P and the pad electrodes A, $A_1$ to $A_n$ are deposited onto the substrate S by vapour-depositing, sputtering or PECVD (plasma-enhanced chemical vapour deposition) and microstructured by photolithographic methods.

The pad electrodes A, $A_1$ to $A_n$ comprise a material with good electrical conductivity, preferably translucent, such as for example indium tin oxide (ITO) or zinc oxide (ZnO).

The light-sensitive elements designed as a continuous layer P can be designed as thin-film photo resistors, photo diodes with PN junctions or PIN junctions or as photo transistors. These may be made in thin-film technology from materials such as for example amorphous silicon (Si), cadmium sulfide (CdS) or cadmium selenide (CdSe).

The contacting electrodes $K_1$ to $K_n$ preferably comprise a biocompatible, conductive material such as for example gold (Au), platinum (Pt), titanium (Ti), iridium (Ir) and are insulated from each other by the biocompatible insulating layer I, for example made from silicon oxide, silicon nitride or polyamide. The contacting electrodes can also be made from translucent material as used for the pad electrodes A, $A_1$ to $A_n$. Equally, the pad electrodes A, $A_1$ to $A_n$ may be made light-impermeable from the same material as the contacting electrodes $K_1$ to $K_n$.

Figure 1B:
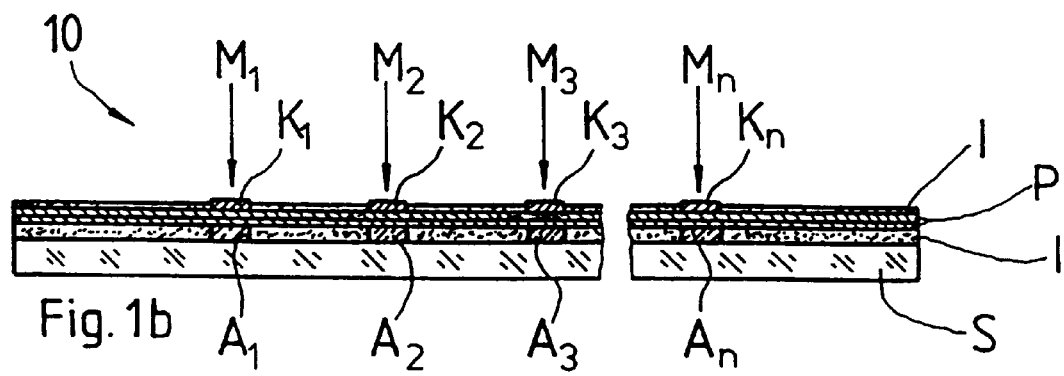

In the embodiment of the invention shown in FIG. 1a, a common lead for all microelectrodes $M_1$ to $M_n$ has been deposited for connection to an electronic device for measuring or stimulation, or similar, at the common continuous pad electrode A, preferably at its marginal area (not shown). In the case of the embodiment of the invention shown in FIG. 1b, the said pad electrodes $A_1$ to $A_n$ insulated from each other, each have their own connecting lead (not shown).

Figure 2A:
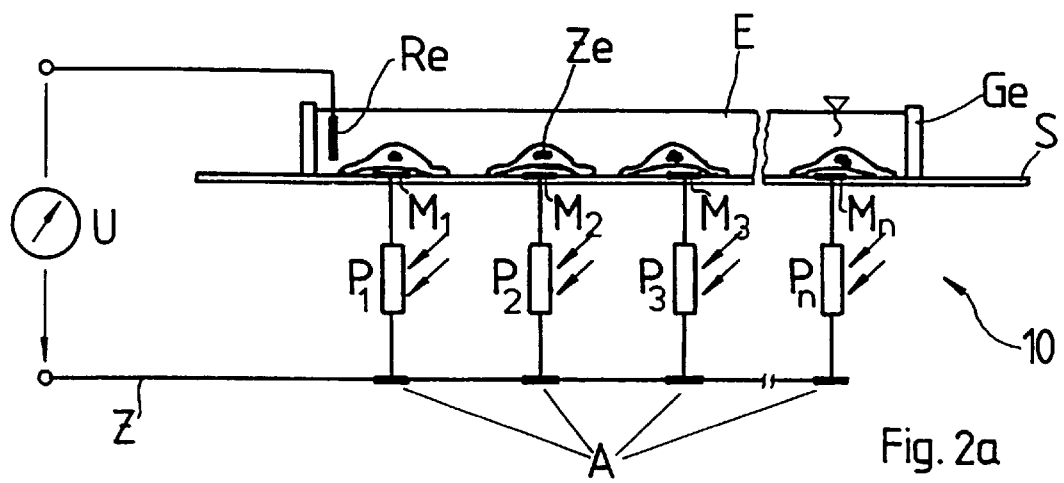
FIG. 2 shows a diagrammatic representation of a microelectrode arrangement according to the invention (FIG. 2a in series, FIG. 2b in parallel)
Figure 2B:
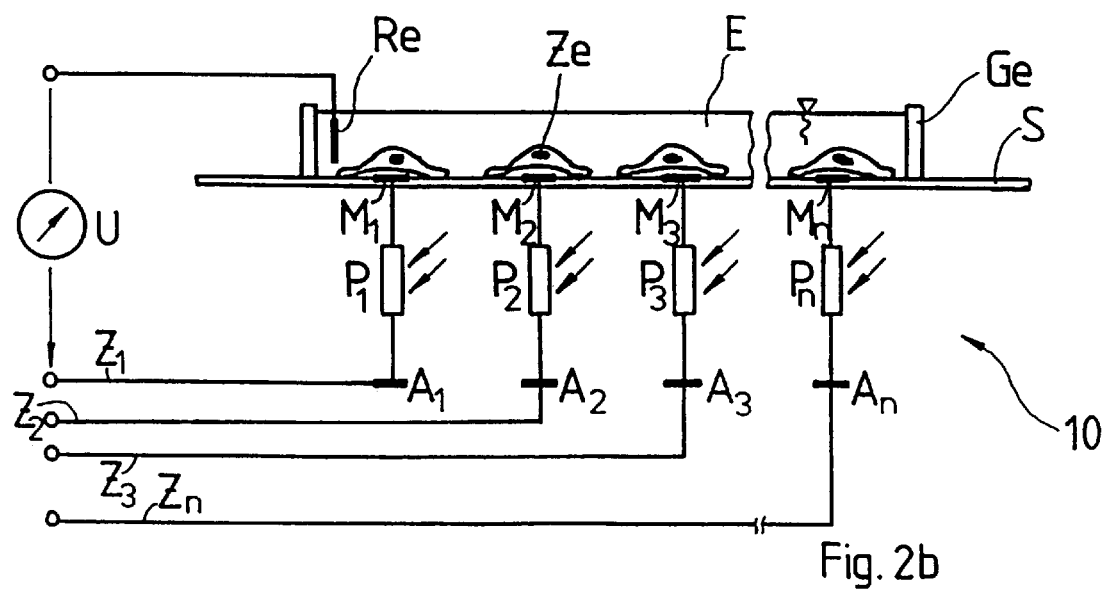

The diagrammatic representation in FIGS. 2a and b shows the application of the microelectrode arrangements 10 from FIGS. 1a and b for leaking electrical cell potentials or for electrical stimulation of networks of biological cells Ze. The biological cells Ze are contained in a cylindrical culture vessel Ge in a physiological electrolyte E. The substrate S with the microelectrode arrangement $M_1$ to $M_n$ from FIGS. 1a and b constitutes the bottom of the culture vessel Ge. In this, the contacting electrodes $K_1$ to $K_n$ not shown in detail in FIGS. 2a and b, are located in close proximity to cell membranes of the cells Ze and are thus each connected to a cell Ze (extracellular connection), in an electrically conducting way via the electrolyte, with an electrical resistance (impedance) present between the cell Ze and the contacting electrode $K_1$ to $K_n$ of the respective microelectrodes $M_1$ to $M_n$.

A reference electrode Re made of metal is immersed into the physiological electrolyte E so that by means of the microelectrodes $M_1$ to $M_n$, an electrical potential can be measured at each desired position in the network of biological cells Ze, or by means of the microelectrodes $M_1$ to $M_n$, the network of biological cells Ze can be electrically stimulated at all desired locations.

The light-sensitive elements $P_1$ to $P_n$ and pad electrodes A, $A_1$ and $A_n$, deposited onto the substrate S, are represented in FIGS. 2a and b with their connecting leads Z, $Z_1$ to $Z_n$ in the form of an electrical circuit diagram.

Figure 3:
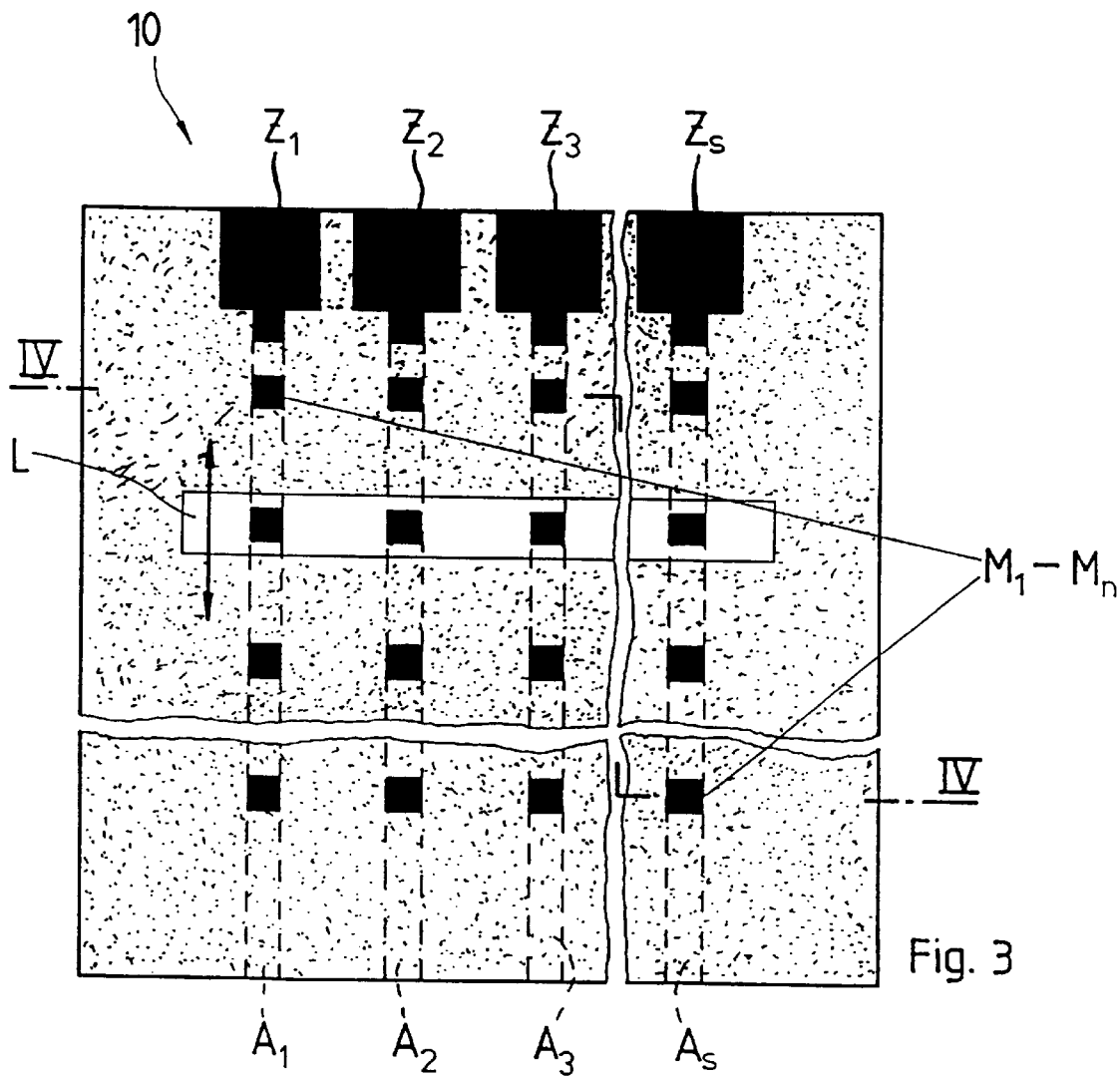
FIG. 3 shows a top view of a microelectrode arrangement according to the invention, with microelectrodes to be switched in a column-parallel way and to be selected in a line-parallel way.
Figure 4:
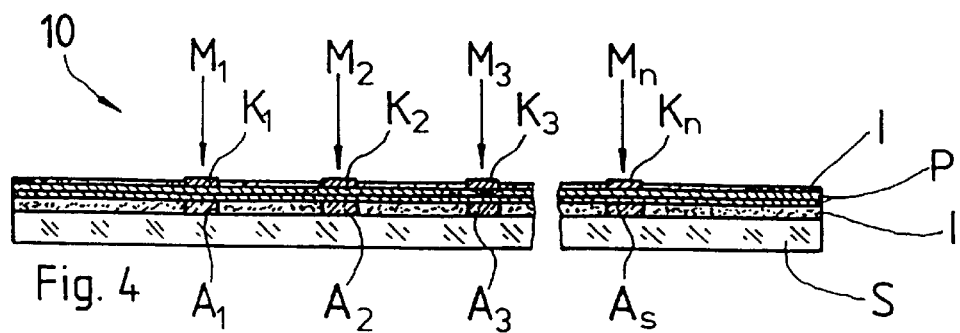
FIG. 4 shows a section along line IV—IV in FIG. 3.

FIGS. 3 and 4 show a microelectrode arrangement 10 according to the invention with microelectrodes $M_1$ to $M_n$ switched in a column-parallel way, where the section according to FIG. 4 corresponds to FIGS. 1a and b. The structure and arrangement of the contacting electrodes $K_1$ to $K_n$ which are insulated from each other by an insulating layer I, and the light-sensitive thin film P corresponds to the above mentioned arrangement, as shown in FIGS. 1a and b. FIG. 3 shows the matrix-shaped arrangement of the micro electrodes $M_1$ to $M_n$. Pad electrodes $A_1$ to $A_n$ are shaped as parallel conducting tracks, continuous in column direction, which on one margin of the substrate S enlarge to become contacting surfaces $Z_1$ to $Z_s$. On the contacting surfaces $Z_1$ to $Z_s$, connecting cables for connecting the microelectrode arrangement 10 to measuring or stimulation electronics are soldered, welded or fixed in some other known way so as to provide electrical conduction. In the embodiment according to FIGS. 3 and 4, the microelectrodes $M_1$ to $M_n$ are brought together into groups comprising a column each. Instead of columns, it is possible, for example, to bring together circles or other groups of microelectrodes $M_1$ to $M_n$.

The pad electrodes $A_1$ to $A_s$ are separated from each other by an insulating layer I. The same materials as mentioned in FIGS. 1a and b can be used as materials for the contacting electrodes $K_1$ to $K_n$, the light-sensitive layer P, the pad electrodes $A_1$ to $A_n$, the insulating layers I and the substrate.

When the microelectrodes $M_1$ to $M_n$ are switched in a column-parallel way, only one microelectrode $M_1$ to $M_n$ of each column can be selected at a given time, i.e. leakage or stimulation can take place. Selection can take place line-by-line or by some other pattern.

Selection of the microelectrode arrangement 10 according to the invention, which selection is shown below in FIG. 3, is by a focussed or shaped light beam or a projected light image which for example is generated by using a laser or provided to the microelectrodes $M_1$ to $M_n$ by means of glass fibres. For selection, the light-sensitive layer P in the region of one or several microelectrodes $M_1$ to $M_n$ to be selected, is illuminated. The illuminated region forms the light-sensitive element of the respective microelectrode $M_1$ to $M_n$. The illuminated region of the light-sensitive layer P becomes electrically conductive, so that the contacting electrodes $K_1$ to $K_n$ of the selected microelectrodes $M_1$ to $M_n$ are connected in an electrically conductive way with the respective pad electrode $A_1$ to $A_s$ and that the electrical potential of a biological cell in close proximity to the respective microelectrode $M_1$ to $M_n$ (FIGS. 2a and b) is leaked, i.e. measured, or that the biological cell can be electrically stimulated.

Selection is either by means of impinging light, i.e. through the network of biological cells, from the direction of the side of the contacting electrodes $K_1$ to $K_n$. In this case, the contacting electrodes $K_1$ to $K_n$ must be translucent or be arranged laterally beside the light-sensitive layer P forming the light-sensitive element which separates the said contacting electrodes $K_1$ to $K_n$ from their pad electrode $A_1$ to $A_s$. Equally, selection can be by transmitted light from the direction of the side of the substrate S. In this case the substrate S and the pad electrodes $A_1$ to $A_s$ must be translucent or arranged beside the light-sensitive layer P forming the light-sensitive element separating them from the contacting electrodes $K_1$ to $K_n$. In the region not illuminated, the thin film P provides insulation. Thus, by locally limited illumination in the region of a microelectrode $M_1$ to $M_n$ in the illuminated region it constitutes the light-sensitive element of this microelectrode $M_1$ to $M_n$.

When using amorphous silicon, resistance ratios of up to five powers of ten between illuminated (bright) and non-illuminated (dark) are attained. With a microelectrode $M_1$ to $M_n$ with a surface of 10 $\mu$m by 10 $\mu$m and a thickness of 0.1 $\mu$m, at a dark conductivity of Sigma=$10^{-9}$ (ohms×cm)$^{-1}$, a dark resistance of $10^{10}$ ½ and with exposure to light, a light resistance of $10^5$ ½. At the surface mentioned of 10 $\mu$m×10 $\mu$m, a contacting electrode $K_1$ to $K_n$, has a resistance through the electrolyte E to the biological cell Ze of also approximately $10^5$ ½; the said resistance being determined by the Helmholtz double layer at the boundary surface metal/electrolyte. With light incidence onto the light-sensitive element P, there is a total transition resistance from the biological cell Ze to the pad electrode $A_1$ to $A_s$ of approx. $2\times10^5$ ½. By contrast, the total transition resistance with a dark light-sensitive element P is approximately $10^{10}$ ½. There is a good contact/separation ratio by the light/dark sampling of the microelectrodes $M_1$ to $M_n$ in respect of their selection.

Since the spacing between the microelectrodes $M_1$ to $M_n$ is large when compared to the layer thickness of the light-sensitive layer P, insulation of the light-sensitive elements constituted by the said light-sensitive layer P from each other is not necessary and it can be constructed in a continuous layer P as described and illustrated. In the embodiment of the invention shown in FIG. 3, selection of the microelectrodes $M_1$ to $M_n$ is by means of a light beam L, aligned in the direction of the line, i.e. transverse to the pad electrodes $A_1$ to $A_s$; the said light beam L illuminates the light-sensitive elements of microelectrodes $M_1$ to $M_n$ which are arranged in a line. Thus the microelectrodes $M_1$ to $M_n$ of a line are selected simultaneously and the electrical cell potentials of the biological cells Ze contacted by these are leaked by way of pad electrodes $A_1$ to $A_s$, or these biological cells Ze are stimulated electrically. The light beam L is mobile in the direction of the column (double arrow in FIG. 3). Selection can of course also take place in various lines, that is not by means of a light beam but by means of individual light spots directed onto individual microelectrodes $M_1$ to $M_n$. In this, from each column, only one microelectrode $M_1$ to $M_n$ can be selected at a given point in time. If the spacing of the microelectrodes $M_1$ to $M_n$ is not sufficient, so that the signals of adjacent microelectrodes $M_1$ to $M_n$ in the region illuminated by the light beam L and thus conductive region of the light-sensitive layer P influence each other, then no continuous light beam L can be used for selecting the microelectrodes $M_1$ to $M_n$. Instead, there must always remain a dark region between the microelectrodes $M_1$ to $M_n$, or else an additional insulating layer must be provided in the light-sensitive layer P (not shown) between the pad electrodes $A_1$ to $A_s$.

In the case of a microelectrode surface of 10 $\mu$m×10 $\mu$m and at 20 $\mu$m electrode spacing, there are for example 60 columns, each with 60 microelectrodes, i.e. a total of 3600 microelectrodes $M_1$ to $M_n$ on a substrate field with a surface of 1.8 mm×1.8 mm.

In the case of a microelectrode arrangement, if applicable, selection of the light-sensitive elements can also be by means of a light-emitting diode matrix as a substrate or by a projected light image.

I claim:

1. A microelectrode arrangement for leaking, with local resolution, electrical cell potentials, or for electrical stimulation of networks of biological cells, with a multitude of microelectrodes, wherein each microelectrode comprises:

a contacting electrode having a first and a second surface and being adapted for electrically contacting the network of biological cells at its first surface;

a pad electrode which is connectable in an electrically conductive way to a measuring device;

a thin-film photoresistor having a first side and a second side and being arranged between the contacting electrode and the pad electrode, said thin-film photoresistor contacting said second surface of said contacting electrode at its first side and contacting said pad electrode at its second side.

2. A microelectrode arrangement according to claim 1, including fiberoptics having at least one optic fiber arranged in front of one of said microelectrodes for emitting light onto said thin-film resistor for optically activating said one of said microelectrodes.

3. A microelectrode arrangement according to claim 2, wherein said fiberoptics comprise a plurality of optical fibers, each one of said microelectrodes having one of said optical fibers associated therewith for optically activating said one of said microelectrodes.

4. A microelectrode arrangement according to claim 3, wherein each optical fiber is associated with a light source for emitting light into said optical fiber.

5. A microelectrode arrangement according to claim 1, wherein a focused light beam is directed in a locally limited way onto a light-sensitive element (P) of at least one microelectrode ($M_n$ to $M_n$).

6. A microelectrode arrangement according to claim 1, wherein selection takes place by at least one of a light-emitting diode matrix as a substrate, and by a projected light image.

7. A microelectrode arrangement according to claim 1, used as an implant.

8. A microelectrode arrangement for leaking, with local resolution, electrical cell potentials, or for electrical stimulation of networks of biological cells, said microelectrode arrangement comprising a multitude of microelectrodes, wherein:

each microelectrode comprises a contacting electrode having a first and a second surface and being adapted for electrically contacting the network of biological cells at its first surface;

a common pad electrode is provided for electrical connection to a measuring device;

a thin-film photoresistor having a first side and a second side is arranged between the contacting electrodes and the common pad electrode, said thin-film photoresistor contacting said second surfaces of said multitude of contacting electrodes at its second side.

9. A microelectrode arrangement according to claim 8, including fiberoptics having at least one optic fiber arranged in front of one of said microelectrodes for emitting light onto said thin-film resistor for optically activating said one of said microelectrodes.

10. A microelectrode arrangement according to claim 9, wherein said fiberoptics comprise a plurality of optical fibers, each one of said microelectrodes having one of said optical fibers associated therewith for optically activating said one of said microelectrodes.

11. A microelectrode arrangement according to claim 9, wherein each optical fiber is associated with a light source for emitting light into said optical fiber.

12. A microelectrode arrangement for leaking, with local resolution, electrical cell potentials, or for electrical stimulation of networks of biological cells, said microelectrode arrangement comprising a multitude of microelectrodes arranged side-by-side, a first plurality of which forming a first group, a second plurality of which forming a second group containing at least one microelectrode, wherein:

each microelectrode comprises a contacting electrode having a first and a second surface and being adapted for electrically contacting the network of biological cells at its first surface;

a common pad electrode adapted for electrical connection to an external device is provided;

at least one pad electrode adapted for electrical connection to an external device is arranged side-by-side to said common pad electrode;

a thin-film photoresistor having a first side and a second side is provided, said thin-film photoresistor having a first section and at least one second section, said first section being arranged between said first group of contacting electrodes and said common pad electrode, said first section contacting said second surfaces of said first group of contacting electrodes at a first side thereof and contacting said common pad electrode at a second side thereof;

each of said second plurality of microelectrodes contacting said at least one second section of said thin-film photoresistor with the second surface of its contacting electrode;

each of said second plurality of microelectrodes being connected to one of said pad electrodes by said at least one second section of said thin-film resistor contacting said at least one pad electrode at the second side thereof.

13. A microelectrode arrangement according to claim 12, including fiberoptics having at least one optical fiber arranged in front of one of said microelectrodes for emitting light onto said thin-film resistor for optically activating said one of said microelectrodes.

14. A microelectrode arrangement according to claim 13, wherein said fiberoptics comprise a plurality of optical fibers, each one of said microelectrodes having one of said optical fibers associated therewith for optically activating said one of said microelectrodes.

15. A microelectrode arrangement according to claim 13, wherein each optical fiber is associated with a light source for emitting light into said optical fiber.

* * * * *